(12) United States Patent
Ames et al.

(10) Patent No.: US 10,993,968 B2
(45) Date of Patent: May 4, 2021

(54) METHODS AND ARTICLES OF MANUFACTURE FOR COSMETIC RESULTS

(71) Applicant: AniCell BioTech, LLC, Chandler, AZ (US)

(72) Inventors: Brandon Ames, Gilbert, AZ (US); Moises Barcelo-Fimbres, Phoenix, AZ (US)

(73) Assignee: ANICELL BIOTECH, LLC, Chandler, AZ (US)

( * ) Notice: Subject to any disclaimer, the term of this patent is extended or adjusted under 35 U.S.C. 154(b) by 399 days.

(21) Appl. No.: 15/473,513

(22) Filed: Mar. 29, 2017

(65) Prior Publication Data

US 2017/0216195 A1    Aug. 3, 2017

Related U.S. Application Data

(63) Continuation-in-part of application No. PCT/US2016/054475, filed on Sep. 29, 2016.

(60) Provisional application No. 62/234,354, filed on Sep. 29, 2015.

(51) Int. Cl.
| | |
|---|---|
| A61K 35/50 | (2015.01) |
| A61K 45/06 | (2006.01) |
| A61K 35/54 | (2015.01) |
| A61K 9/00 | (2006.01) |
| A61K 9/08 | (2006.01) |
| A61K 8/02 | (2006.01) |
| A61K 8/98 | (2006.01) |
| A61Q 19/08 | (2006.01) |
| A61K 9/06 | (2006.01) |
| A61L 15/40 | (2006.01) |
| A61L 15/44 | (2006.01) |
| A61L 27/26 | (2006.01) |
| A61L 27/36 | (2006.01) |
| A61L 27/38 | (2006.01) |
| A61L 27/54 | (2006.01) |

(52) U.S. Cl.
CPC ............ *A61K 35/50* (2013.01); *A61K 8/0212* (2013.01); *A61K 8/0241* (2013.01); *A61K 8/982* (2013.01); *A61K 9/0019* (2013.01); *A61K 9/0048* (2013.01); *A61K 9/0051* (2013.01); *A61K 9/06* (2013.01); *A61K 9/08* (2013.01); *A61K 35/54* (2013.01); *A61K 45/06* (2013.01); *A61L 15/40* (2013.01); *A61L 15/44* (2013.01); *A61L 27/26* (2013.01); *A61L 27/3604* (2013.01); *A61L 27/3804* (2013.01); *A61L 27/54* (2013.01); *A61Q 19/08* (2013.01); *A61K 2800/412* (2013.01)

(58) Field of Classification Search
CPC ..... A61K 35/50; A61K 8/0212; A61K 8/0241
See application file for complete search history.

(56) References Cited

U.S. PATENT DOCUMENTS

| | | | | |
|---|---|---|---|---|
| 2004/0048796 | A1* | 3/2004 | Hariri | A61K 35/50 424/423 |
| 2008/0181967 | A1* | 7/2008 | Liu | A61K 35/44 424/583 |
| 2008/0286378 | A1 | 11/2008 | Behrens et al. | |
| 2009/0306163 | A1* | 12/2009 | Lipkin | A61Q 19/08 514/390 |
| 2011/0158958 | A1 | 6/2011 | Sing | |
| 2011/0293667 | A1 | 12/2011 | Baksh et al. | |
| 2013/0039896 | A1 | 2/2013 | Smith et al. | |
| 2016/0263281 | A1* | 9/2016 | Koob | A61K 9/14 |

FOREIGN PATENT DOCUMENTS

| | | | | |
|---|---|---|---|---|
| WO | WO2015195506 | * | 6/2014 | |
| WO | 2014152234 | | 9/2014 | |
| WO | WO2014152234 | * | 9/2014 | ............. A61K 35/50 |

OTHER PUBLICATIONS

International Search Report dated Dec. 20, 2016 in PCT Application No. PCT/US2016/054475.
International Preliminary Report on Patentability dated Apr. 12, 2018 in PCT Application No. PCT/US2016/054475.
Zuo et al. "Regeneration of mature dermis by transplanted particulate acellular dermal matrix in a rat model of skin defect wound," J Mater Sci: Mater Med, Aug. 19, 2012 (Aug. 19, 2012), vol. 23, pp. 2933-2944.
CIPO; Non-Final Office Action dated Feb. 14, 2019 in CA Application No. 3000401.
CIPO; Office Action dated Apr. 20, 2020 in CA Application No. 3000401.
USPTO; Restriction Requirement dated Jun. 22, 2020 in U.S. Appl. No. 15/764,275.
USPTO; Non-Final Office Action dated Aug. 4, 2020 in U.S. Appl. No. 15/764,275.
USPTO; Final Office Action dated Dec. 7, 2020 in U.S. Appl. No. 15/764,275.
Osetsky et al. "Cryogenic Technologies in Production of Pharmaceutical, Cosmetic, Agrotechnical Formulations and Biologically Active Food Additives." Problems of Cryobiology and Cryomedicine 19.4 (2009): 488-499 (Year: 2009).

* cited by examiner

*Primary Examiner* — Blaine Lankford
(74) *Attorney, Agent, or Firm* — Snell & Wilmer L.L.P.

(57) ABSTRACT

Methods are disclosed for the collection and processing of amniotic material in animals. These methods involve collection of amniotic material directly during parturition or cesariean section in animals for the processing of regenerative wound treatments and tissue repairs without culturing or utilization of any excess manipulation of tissue. These materials are used to effect a cosmetic result.

13 Claims, 4 Drawing Sheets

METHODS AND ARTICLES OF MANUFACTURE FOR COSMETIC RESULTS

CROSS REFERENCE TO RELATED APPLICATIONS

This application claims priority to and is a continuation in part of International Application No. PCT/US2016/054475, filed Sep. 29, 2016, entitled "Methods and Articles of Manufacture for the Treatment of Animals," which claims priority to and benefit of U.S. Provisional Patent Application No. 62/234,354, filed Sep. 29, 2015, of the same title. The contents of these applications are incorporated herein by reference in their entirety.

STATEMENT REGARDING FEDERAL SPONSORSHIP

Inventions described herein were not conceived or reduced to practice with Federal sponsorship.

FIELD OF THE INVENTION

The present disclosure provides processed fetal tissues and cells suitable for reducing the effects of aging seen on skin and methods of using these fetal tissues and cells to promote a cosmetically appealing aspect to skin.

BACKGROUND OF THE INVENTION

The effects of aging on the human skin produce cosmetically undesirable appearance. These effects include wrinkles, creases, sags, hair loss, spots, loss of flexibility, thinning, loss of color and others. These effects are often addressed with surgical intervention such as face lifts, dermal fillers, onabutulinumtoxinA (sold under the tradename BOTOX®, Allergan, Inc., Irvine, Calif.). However, these interventions subject the subject receiving the intervention with risks and the effects may be of short duration, incomplete or produce unsatisfactory results.

It would be useful to have methods and articles of manufacture that reduce the undesirable effects of aging on skin. As used herein, unless the context requires otherwise, the term "subject" encompasses and includes humans and animals receiving intervention for the effects of aging on skin.

SUMMARY OF THE INVENTION

Embodiments of the present invention feature methods and articles of manufacture that reduce the effects of aging on skin in humans and in animals.

The fetal tissue and cellular compositions disclosed herein have many advantages for use in intervening with normal aging processes including promoting healing of injuries, immune privilege, an absence of associated ethical issues, and no requirement of invasive procedures for harvesting the cells and tissues. In addition, the treatment regimen disclosed herein is remarkably effective at promoting the rapid healing of open wounds within one to two weeks.

One embodiment is directed to an article of manufacture. The article comprises aesthetic modifier comprising a dried particulate mixture of mechanically decellularized amnion obtained from one or more animals compatible with a subject animal. The dried particulate mixture is capable of reconstitution to form a reconstituted aesthetic modifier for administration to the subject animal to produce a cosmetic result.

By way of example, without limitation, a cosmetically effective amount of the reconstituted medicament is applied by injecting at or around the periphery of or under or into wrinkles, creases, sags, hair loss, spots, loss of flexibility, thinning, loss of color and others, or applied to a subject by way of dropper or spray, cream, ointment, slurry, paste, wash, mask, dermal patch, powder, solution or suspension to the skin of a subject or into a dermal layer of the skin of a subject, or the like to a cosmetic result. As used herein, the term "cosmetic result" means a aesthetically pleasing result suggesting a more youthful or healthy appearance. Such appearance can mean one or more of the following including fuller skin, decreased appearance of wrinkles, creases, sagging, hair loss and spots, greater flexibility, healthier color, hair regeneration and the like. As used herein, the term "subject" refers to the person or animal receiving the aesthetic modifier.

In one aspect, one milliliter of reconstituted aesthetic modifier is the amount of particulate matter obtained from the mechanically decellularized amnion of about $1.5 \; 10^{-2}$ cm$^3$ to $5 \; 10^{-2}$ cm$^3$ of amnion. In one aspect, the mechanically decellularized amnion is filtered to contain particles of less than about 100 microns in diameter.

Embodiments of the present invention feature a particulate mixture comprising particles. The particles have an approximate diameter of less than 500µ, or less than 400µ, or less than 300µ, or less than 200µ, or less than 150µ, or less than 100µ, or less 90µ, or less than 80µ, or less than 70µ, or less than 60µ, or less than 50µ, or less than 40µ, or less than 30µ, or less than 20µ, or less than 10µ. In other embodiments, the particles have a diameter of more than 10µ, or more than 20µ, or more than 30µ, or more than 40µ, or more than 50µ, or more than 60µ, or more than 70µ, or more than 80µ, or more than 90µ, or more than 100µ, or more than 200µ, or more than 300µ, or more than 400µ, or more than 500µ. In other embodiments, the particles have an approximate diameter of about 500µ, or about 400µ, or about 300µ, or about 200µ, or about 150µ, or about 100µ, or about 50µ, or about 25µ.

In certain embodiments, the article comprises a dried particulate mixture of mechanically decellularized amnion obtained from one or more animals compatible with a subject, and fetal cells obtained from one or more animals compatible with a subject to form a particulate cellular suspension. The particulate cellular suspension is administered to a subject to produce a cosmetic result.

By way of example, without limitation, a cosmetically effective amount of the aesthetic modifier comprising a particulate cellular suspension medicament can be injected around the periphery of or under or into wrinkles, creases, sags, hair loss, spots, loss of flexibility, thinning, loss of color and others, or applied to a subject by way of dropper or spray, cream, ointment, slurry, paste, wash, mask, dermal patch, powder, solution or suspension to the skin of a subject or into a dermal layer of the skin of a subject, or the like to a cosmetic result.

A cosmetically effective amount of the particulate cellular suspension medicament comprises about $10^1$ to $10^{20}$ cells per mL. Other embodiments feature about $10^3$ to about $10^7$ cells per mL.

A further embodiment of the article further comprises a fetal tissue wrap. The tissue wrap can comprise amnion tissue obtained from one or more animals compatible with a subject. The wrap is constructed and arranged for placement in juxtaposition with a site of wrinkles, creases, sags, hair loss, spots, loss of flexibility, thinning, loss of color to promote a cosmetic result. For facial applications, the wrap is shaped or contoured to the shape and contour of the face.

The wrap, comprising fetal tissue, can be air-dried for about 1 minute to about 48 or more. In another embodiment, the wrap is air-dried for about 1 hour to about 12 hours. In another embodiment, the wrap is air-dried for about 1 hour to about 6 hours. In another embodiment, the wrap is air-dried for about 1 hour to about 3 hours. In another embodiment, the wrap is air-dried for about 1 hour to about 2 hours.

In another aspect of the invention, one embodiment features a kit for producing a cosmetic result in a subject. One kit comprises aesthetic modifier comprising a dried particulate mixture of mechanically decellularized amnion obtained from one or more animals compatible with a subject. The aesthetic modifier is directly applied or incorporated in one or more of the carriers such as a spray, cream, ointment, slurry, paste, wash, mask, dermal patch, powder, solution or suspension. The dried particulate mixture may be held as a powder that can be capable of reconstitution to form a reconstituted aesthetic modifier.

A further embodiment of the kit comprises fetal cells obtained from one or more animals compatible with a subject that are compatible with a particulate mixture obtained from the mechanical decellularization of amnion isolated from one or more animals. The fetal cells are applied in cooperation or concurrently with the reconstituted aesthetic modifier or form a combined aesthetic modifier comprising a particulate cellular suspension and/or amniotic liquid for administration to the subject to produce a cosmetic result.

A further embodiment of the kit comprises a tissue wrap obtained from one or more animals compatible with a subject. The tissue wrap comprises amnion tissue constructed and arranged for placement in juxtaposition with the site of wrinkles, creases, sags, hair loss, spots, loss of flexibility, thinning, loss of color to promote a cosmetic result. The tissue wrap is applied in cooperation or concurrently with the reconstituted aesthetic modifier or a combined medicament comprising a particulate cellular or acellular suspension medicament with or without mechanically decellularized amnion and/or amniotic liquid for administration to the subject to produce a cosmetic result.

A further embodiment of the present invention features an inflammation inducing means selected from the group comprising keratolytics, irritants, rubefacients, abrasives, phototherapy, dermal microneedle devices for application prior to or during administration of the aesthetic modifier. For example, without limitation, one or more keratolytics, irritants, rubefacients, or abrasives are carried in a spray, cream, ointment, slurry, paste, wash, mask, dermal patch, powder, solution or suspension for application before or carried with the aesthetic modifier and applied with the aesthetic modifier.

A further embodiment of the present invention is directed to a method of producing a cosmetic result in a subject. One embodiment of the present method features the steps of administering to the site of wrinkles, creases, sags, hair loss, spots, loss of flexibility, thinning, loss of color an injury at least one of the group consisting of a reconstituted aesthetic modifier, a reconstituted amnion suspension with or without cells and a tissue wrap all of which have been previously described.

For example, without limitation, in one embodiment, a method comprises the step of applying a reconstituted aesthetic modifier. The reconstituted aesthetic modifier is made from a dried particulate mixture of mechanically decellularized amnion obtained from one or more animals compatible with a subject.

Another method features the step of applying, by way of injection, an aesthetic modifier comprising a particulate cellular suspension medicament to the periphery or under or into the site of wrinkles, creases, sags, hair loss, spots, loss of flexibility, thinning, loss of color to promote a cosmetic result. The particulate cellular suspension comprises particles derived from the mechanical decellularization of amnion obtained from one or more animals compatible with the subject animal, and isolated amniotic fluid cells obtained from the one or more animals compatible with the subject.

In one aspect, the method further comprises the step of applying a tissue wrap to the site wrinkles, creases, sags, hair loss, spots, loss of flexibility, thinning, loss of color to promote a cosmetic result. The wrap comprises amnion tissue compatible with the subject constructed and arranged for placement in juxtaposition with the site of wrinkles, creases, sags, hair loss, spots, loss of flexibility, thinning, loss of color. The amnion tissue is air-dried for about 1 minute to about 48 hours or more. In another embodiment the amnion tissue is air-dried for about 1 hour to about 12 hours. In another embodiment, the amnion tissue is air-dried for about 1 hour to about 6 hours. In another embodiment, the amnion tissue is air-dried for about 1 hour to about 3 hours. In another embodiment, the amnion tissue is air-dried for about 1 hour to about 2 hours. One embodiment features a wrap shaped to the contours of the face for facial application in the nature of a mask.

In one aspect of the method, the site of wrinkles, creases, sags, hair loss, spots, loss of flexibility, thinning, loss of color to promote a cosmetic result is prepared prior to or with the applying of one or more of the group consisting of a cellular reconstituted suspension, or a reconstituted acellular suspension medicament and a tissue wrap. The preparation creates an inflammation response which improves the effectiveness of the aesthetic modifier. For example without limitation, an inflammation inducing means selected from the group comprising keratolytics, irritants, rubefacients, abrasives, phototherapy, dermal microneedle devices is applied prior to or during administration of the aesthetic modifier. The one or more keratolytics, irritants, rubefacients, or abrasives are carried in a spray, cream, ointment, slurry, paste, wash, mask, dermal patch, powder, solution or suspension for application before or carried with the aesthetic modifier and applied with the aesthetic modifier.

A further embodiment is directed to a method of making a dried particulate mixture of mechanically decellularized fetal tissue obtained from one or more animals compatible with a subject. The dried particulate mixture is capable of reconstitution to form a reconstituted medicament for administration to the subject to produce a cosmetic result. The method comprises the step of mechanically decellularizing amnion tissue to form particles capable of reconstitution.

A further embodiment is directed to a method of making a aesthetic modifier comprising a particulate cellular suspension. The method comprises the steps of providing a dried particulate mixture of mechanically decellularized amnion obtained from one or more animals compatible with a subject, and fetal cells obtained from one or more animals compatible with a subject animal and forming a particulate cellular suspension. The aesthetic modifier comprising a particulate cellular suspension is administered to a subject to produce a cosmetic result.

A further embodiment of the present invention features methods of making a tissue wrap, a particulate mixture medicament and a particulate cellular suspension medicament. One embodiment of the method of making the tissue wrap comprises the steps of applying amnion tissue to a support to form a supported amnion. The supported amnion is next air dried to form the tissue wrap which is placed in a suitable containment means until applied. One embodiment features a mask. The mask is formed by shaping the wrap to the contours of the face.

A further embodiment is directed to a method of making an aesthetic modifier for effecting a cosmetic result comprising the steps of mechanically decellularizing fetal tissue obtained from one or more animals compatible with a subject animal and drying the decellularized fetal tissue to form a dried particulate mixture for reconstitution and administration.

These and other features and advantages will be apparent upon viewing the Figures that are briefly described below and upon reading the detailed description that follows.

DETAILED DESCRIPTION

Unless otherwise defined herein, scientific and technical terms used herein have the meanings that are commonly understood by those of ordinary skill in the art. In the event of any latent ambiguity, definitions provided herein take precedence over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

It is noted here that as used in this specification and the appended claims, the singular forms "a", "an", and "the" also include plural reference, unless the context clearly dictates otherwise.

The term "about" or "approximately" means within 10%, and more preferably within 5% (or 1% or less) of a given value or range.

As used herein, the term "isolated cell" refers to a cell that has been removed from its in-vivo location.

As used herein, the term "decellularization" refers to a process that removes cells from a tissue while preserving the native ultrastructure and composition of the extracellular matrix (ECM). For example, an amnion particulate mixture can be obtained by decellularizing a fetal tissue comprising amnion.

There are a number of methods of decellularization of tissue known in the art, including, but not limited to, chemical agents, hypotonic and hypertonic solutions, detergents (e.g., Triton-X), alcohols, solvents (e.g., tributyl phosphate (TBP), biologic agents (e.g., collagenase, trypsin, lipase, nucleases, α-galactosidase), non-enzymatic agents (e.g., chelating agents such as EDTA or EGTA), physical agents (e.g., temperature, force and pressure, non-thermal irreversible, mechanical, electroporation (NTIRE) (see, for example, Crapo et al., Biomaterials. 2011; 32(12): 3233-3243). In certain embodiments, one or a combination of the aforementioned methods may be used to decellularize a tissue. However, methods that preserve the complex composition and three-dimensional ultrastructure of the extracellular matrix (ECM) are preferred.

In one embodiment, a tissue is mechanically decellularized, e.g., by cryofractionation, a procedure in which a tissue is frozen and ground in a cryomill to produce a mixture of particles. Such particles are obtained from the cryofractionation of about 0.5 cm², or about 1 cm², or about 1.5 cm², or about 2 cm², or about 2.5 cm², or about 3 cm², or about 3.5 cm² or about 4 cm², or about 4.5 cm² to about 5 cm² of amnion or more. The amnion can have a thickness of from about 500 μm to 50 μm or from 400 μm to about 50 μm, or from about 300 μm to 50 μm or from about 200 μm to about 50 μm or from about 150 μm to about 50 μm from about 100 μm to about 50 μm or from about 50 μm to about 25 μm or less. In another embodiment the amnion has a thickness of about 500 μm or about 400 μm or about 300 μm or about 200 μm or about 150 μm or about 100 μm or about 50 μm or about 25 μm or less.

As used herein, 1 μm refers to a micrometer or 10⁻⁶ meters.

The term "amnion" refers to a thin, cellular, extra-embryonic membrane that forms the inner membrane of a closed sac surrounding and protecting an embryo in reptiles, birds, and mammals. The sac contains the fetus and amniotic fluid, in which the embryo is immersed, nourished and protected. Typically, the amnion is a tough, transparent, nerve-free, and nonvascular membrane consisting of two layers of cells: an inner, single-cell-thick layer of ectodermal epithelium and an outer covering of mesodermal, connective, and specialized smooth muscular tissue. In the later stages of pregnancy, the amnion expands to come in contact with the inner wall of the chorion creating the appearance of a thin wall of the sac extending from the margin of the placenta. The amnion and chorion are closely applied, though not fused, to one another and to the wall of the uterus. Thus, at the later stage of gestation, the fetal membranes are composed of two principal layers: the outer chorion that is in contact with maternal cells and the inner amnion that is bathed by amniotic fluid. The amnion has multiple functions, e.g., as a covering epithelium, as an active secretary epithelium, and for intense intercellular and transcellular transport.

As used herein, the term "tissue" refers to an aggregate of similar cells and associated extracellular matrix (ECM) forming a definite kind of organized material with a specific function, in a multicellular organism.

As used herein, an "amnion tissue" refers to the isolated cellular, extra-embryonic amnion membrane that is detached from the chorion. In one embodiment, the amnion tissue is air-dried. In another embodiment, the amnion is air-dried for about 60 to about 90 minutes or more at ambient temperature (i.e. about 18 to 24° C.).

As used herein, a "particulate mixture" refers to the powder or particles obtained from the cryofractionation of amnion.

As used herein, the term "fetal tissue" refers to extra-embryonic tissues including, but not limited to, amnion, chorion, yolk sac, the allantois, umbilical cord and/or fetal placenta (villous chorion).

As used herein, the term "fetal cells" refers to cells resident in the extra-embryonic tissues including, but not limited to, amnion, chorion, yolk sac, the allantois, umbilical cord, fetal placenta (villous chorion) and/or amniotic fluid. In certain embodiments, the term "fetal cells" refer to isolated fetal cells.

In certain embodiments, the term "fetal cells" refers to unfractionated cells of the amniotic fluid including epithelial and/or amniotic fluid or membrane-derived mesenchymal stem cells (see U.S. Patent Publication No. US 2013/0230924, which is incorporated by reference herein in its entirety).

The term "injury" means a pathological condition, such as, by way of example, without limitation, a wound, incision, a break in the skin, bone, tendon, ligament, muscle, neoplasia, eye, and soft tissues, an inflammation, infection, or other disease condition.

The term "promoting healing" refers to causing a favorable result compared to no treatment. The favorable result comprises any one or more of the following such as reduction of scarring, reduction of inflammation, regrowth of normal tissue or growth of scar tissue, improved load bearing on a limb movement, closure of wound, reduction in infection and reduction in mortality associated with the underlying pathology.

The term "aesthetic modifier" refers to a material that produces a cosmetic effect on skin. This effect is not clearly a healing of an injury but is in the nature of ordinary and common aging, or exposure to long-term environmental conditions such as light. As used herein, the term "cosmetic effect" refers to a more pleasing younger appearance, in the nature of fewer or shallower wrinkles or creases, less sagging, less hair loss, hair regeneration, tighter fuller skin, thicker and more flexible skin, improved coloring, fewer or smaller or lighter spots.

The term "compatible with a subject" denotes the origin of the tissue as being from the same species or closely related species or a species that does not elicit a strong immune response.

In other embodiments, the term "compatible with a subject" refers to an xenograft, i.e., a tissue graft from different species.

In another embodiment, the term "compatible with a subject" refers to allografts, i.e., a tissue from one individual to another of the same species with a different genotype.

As used herein, an "animal" refers to living multi-cellular vertebrate organisms, a category that includes, for example, mammals, birds, reptiles, and amphibians. The term mammal includes both human and non-human mammals. Similarly, the term "subject" includes both human and non-human subjects. In a cosmetic sense, the term "subject" refers to an individual human which has a site having wrinkles, creases, sags, hair loss, spots, loss of flexibility, thinning, loss of color or other effects of aging.

As used herein, a non-human animal can refer to a mammal including, but not limited to, a domesticated animal such as a dog, a racing dog, sheep, a pig, a goat, cattle, a zebu, a cat, a guinea pig, a donkey, water buffalo, including "river buffalo" and "swamp buffalo", a horse, a racing horse, a dromedary camel, a yak, a bactrian camel, a llama, an alpaca, a ferret, a mouse, a bali cattle, a gayal, a rabbit, a rat and a lab rat, a silver fox or a hedgehog.

In certain embodiments, a non-human animal can refer to mammals kept in zoos including, but not limited to, zebra, gazelle, wolves, wild swine (pigs & hogs), wild cattle, warthogs, vervet monkeys, two-toed sloths, tree pangolins, tigers, tapirs, tamandua or lesser anteaters, takins, sun bears, striped hyena, spotted hyena, spiral-horned antelope, somali wild ass, snow leopards, small cats, sloth bears, singing dogs, siamang, serval, sea lions, rock hyrax, rhinoceros, reindeer, red pandas, pygmy marmosets, pygmy hippopotamus, przewalski's horses, pronghorns, prairie dogs, porcupines, polar bears, painted dogs, otters, oryx, orangutan, okapi, ocelot, nubian ibex, nile lechwe, naked mole-rats, mountain lions (puma, cougar), monkeys, meerkat, mangabey, mandrill, lynx and bobcats, lions, leopards, lemur, jaguars, honey badgers (ratel), hippos, hamadryas baboons, guenon, guanaco, gorillas, giraffe, giant pandas, giant anteaters, gelada baboons, fossa, fishing cats, elephants, echidna, dhole, coquerel's sifaka, clouded leopards, chimpanzees, cheetahs, tigers, caracals, capybara, camels, brown bears, bonobos, binturongs, bat-eared fox, bats, armadillos, antelope, andean (spectacled) bears, birds and agouti.

In certain other embodiments, a non-human animal can refer to mammals considered by the World Wildlife Fund to be endangered including, but not limited to, the amur leopard, black rhino, cross river gorilla, javan rhino, mountain gorilla, pangolin, saola, south china tiger, sumatran elephant, sumatran orangutan, sumatran rhino, sumatran tiger, vaquita, western lowland gorilla, yangtze finless porpoise, african wild dog, amur tiger, asian elephant, bengal tiger, black spider monkey, black-footed ferret, blue whale, bonobo, bornean orangutan, borneo pygmy elephant, chimpanzee, eastern lowland gorilla, fin whale, ganges river dolphin, giant panda, hector's dolphin, indian elephant, indochinese tiger, indus river dolphin, malayan tiger, north atlantic right whale, orangutan, sea lions, sei whale, snow leopard, Sri Lankan elephant, tigers and whales.

In certain embodiments, a non-human animal can refer to marsupials, including, but not limited to, wallabies, koalas, possums, opossums, kangaroos, bandicoots, wombats, bettongs, bilbys, quolls, quokkas and the Tasmanian devil.

The term "reconstituted" means that that an aqueous liquid is added to make the material. A liquid for reconstitution comprises a biocompatible solution such as normal saline, e.g. phosphate buffered saline (PBS) or amniotic fluid. A preferred liquid for reconstitution is calcium-free sterile, non-pyrogenic isotonic solution suitable for intravenous administration. For example, without limitation, one such liquid is sold under the trademark PlasmaLyte A™ in a single dose container for intravenous administration. Each 100 mL contains 526 mg of Sodium Chloride, USP (NaCl); 502 mg of Sodium Gluconate ($C_6H_{11}NaO_7$); 368 mg of Sodium Acetate Trihydrate, USP ($C_2H_3NaO_2.3H_2O$); 37 mg of Potassium Chloride, USP (KCl); and 30 mg of Magnesium Chloride, USP ($MgCl_2.6H_2O$). It contains no antimicrobial agents. The pH is 7.4.

The term "administering" means applying or injecting or ingesting the material. The term "applying" is used broadly and includes uses such as washes, placing and massaging into the skin as performed with conventional creams, ointments lotions and pastes and implantation.

Connective soft tissue defects or injuries often occur by damage to the extra-cellular matrix (ECM) that forms muscles, ligaments or tendons in mammals. Collagen is the most abundant structural protein in the connective tissue (ECM) and acts as a natural scaffold for cellular attachment in the body.

Amnion is an abundant source of collagen, as well as the other proteins, carbohydrates, lipids, hyaluronic acid, laminin, fibronectin, pluripotent mesenchymal stem cells (MSC) and other complex growth factors that are essential for fetal growth and development. In particular, amnion has a complete lack of surface antigens, thus it does not induce an immune response when implanted into a 'foreign' body, which is in contrast to most other allograft implants. Amnion also markedly suppresses the expression of the pro-inflammatory cytokines, IL-1α and IL-1β (Solomon et al., 2001, Br. J. Ophthalmol. 85 (4):444-9) and produces natural inhibitors of matrix metalloproteases (MMPs) expressed by infiltrating polymorphonuclear cells and macrophages (Hao et al., 2000, Cornea, 19 (3):348-52; Kim et al., 2000, Exp. Eye Res. 70 (3):329-37). Amnion also down-regulates TGF-β and its receptor expression by fibroblasts leading to the ability to modulate the healing of a wound by promoting tissue reconstruction. Furthermore, amnion has a broad spectrum of antimicrobial activity against bacteria, fungi, protozoa, and viruses for reduced risk of post-operative infection.

Amnion derived tissues are therefore immune-privileged and ideally suited for cosmetic purposes.

A "kit" is an assembly of parts, materials, and compositions of matter packaged together to facilitate a procedure. Kits commonly comprise instructions for the use of the parts, materials and compositions.

Figure 1:
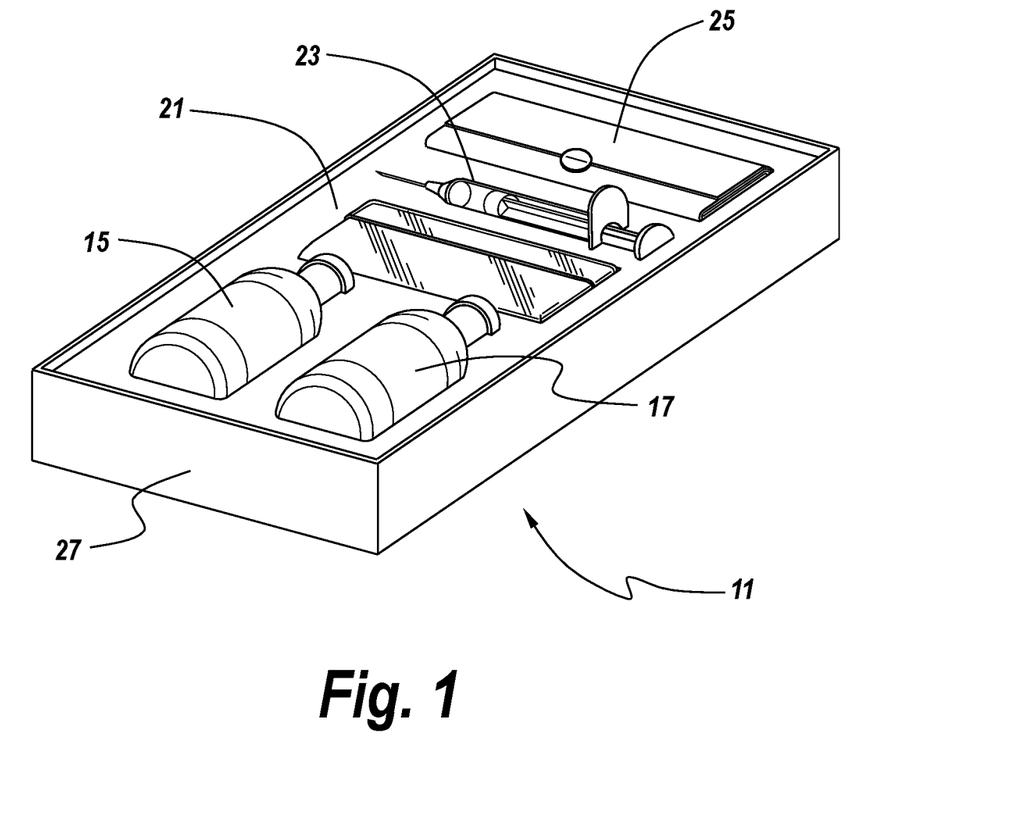
FIG. 1 depicts a kit embodying features of the present invention.

Turning now to FIG. 1, a kit embodying features of the present invention, generally designated by the numeral 11 is depicted. Kit 11 has the following major elements: a first vial 15, a second vial 17, a container for a tissue wrap 21, a syringe 23, and instructions 25. The kit 11 is held in suitable packaging, as depicted, a box 27. Suitable packaging may comprise any means for holding the collection of parts, materials and compositions. For example, without limitation, bags, wraps, containers, ties and the like.

The first vial 15 contains a aesthetic modifier comprising a dried particulate mixture of mechanically decellularized amnion obtained from one or more animals compatible with a subject. Upon reconstitution, the aesthetic modifier forms a reconstituted aesthetic modifier. The kit 11 may contain a vial containing such liquid for reconstitution [not shown] or the liquid for reconstitution may be derived from other sources.

The second vial contains fetal cells obtained from one or more animals compatible with a subject and compatible with a particulate mixture in the first vial 15. The fetal cells are applied in cooperation or concurrently with the reconstituted aesthetic modifier or form a combined aesthetic modifier comprising a particulate cellular suspension and fetal cells for application to the subject to produce a cosmetic effect. In forming a combined aesthetic modifier, the dried particulate mixture of the first vial 15 is reconstituted with or combined with the fetal cells of the second vial 17, supplemented as needed with further liquid for reconstitution. For example, the dried particulate mixture can be reconstituted by suspension in a solution of 50% solution for reconstitution, such as PlasmaLyte A', and 50% amniotic fluid containing fetal cells.

The combined aesthetic modifier is injected into or around the site of at least one of the group of sites comprising creases, wrinkles, inconsistent pigment, sags, hair loss, spots, loss of flexibility, thinning, and voids injury with syringe 23.

The kit 11 may also contain cream or ointment or lotion or paste bases in a third vial or jar [not shown] to which the combined aesthetic modifier and/or the aesthetic modifier comprising the dried particulate cellular and/or the reconstituted aesthetic modifier is incorporated by agitation and or levigation. Cream and lotion bases are sold under a variety of tradenames such as Eucerin® and Nivea® (Beiersdorf, Inc., Hamburg, Germany). Ointment bases are sold under a number of tradenames and comprise white petrolatum as a major constituent. Pastes can be made readily by adjusting the water content of the fluids used for reconstitution or by adding inert builders such as carboxymethycellulose. The cream, lotion, ointment or paste can be made just prior to application or premade. Although reference is made to commercially available cream and ointment bases, the aesthetic modifier, reconstituted aesthetic modifier and combined aesthetic modifier may be incorporated in similar creams, ointments, lotion and pastes during the manufacture of the base.

The kit 11 may also contain an inflammation inducing means {not shown]. Inflammation inducing means creates an inflammation creates an inflammation response which improves the effectiveness of the aesthetic modifier. For example without limitation, a inflammation inducing means selected from the group comprising keratolytics, irritants, rubefacients, abrasives, phototherapy, dermal microneedle devices is applied prior to or during administration of the aesthetic modifier. The one or more keratolytics, irritants, rubefacients, or abrasives are carried in a spray, cream, ointment, slurry, paste, wash, mask, dermal patch, powder, solution or suspension held in a vial [not shown] similar to the vials depicted or in a jar. The one or more keratolytics, irritants, rubefacients, or abrasives are applied before or carried with the aesthetic modifier and applied with the aesthetic modifier. Irritants, rubefacients and vesicants are know in the art and include, by way of example, without limitation, anthralin, camphor, cantharidin, *capsicum*, coal tar, ichthammol, juniper tar, menthol, Peruvian balsam, and pine tar. Keratolytics are known in the art and include by way of example, without limitation, benzoyl peroxide, salicylic acid, retinoic acid and other vitamin A derivatives. Keratolytic compounds are commonly found in acne treatment products. The kit 11 may also comprise photo or light devices to create an inflammatory response. Photo or light devices are known in the art as sun lamps and tuned lazer devices.

The container for a tissue wrap 21 contains a tissue wrap derived from amnion tissue obtained from one or more animals compatible with a subject. The tissue wrap comprises amnion tissue constructed and arranged for placement in juxtaposition with at least one of the group of sites comprising creases, wrinkles, inconsistent pigment, sags, hair loss, spots, loss of flexibility, thinning, and voids. The tissue wrap is applied in cooperation or concurrently with the aesthetic modifier, reconstituted aesthetic modifier or a combined aesthetic modifier to create a cosmetic result.

Figure 2:
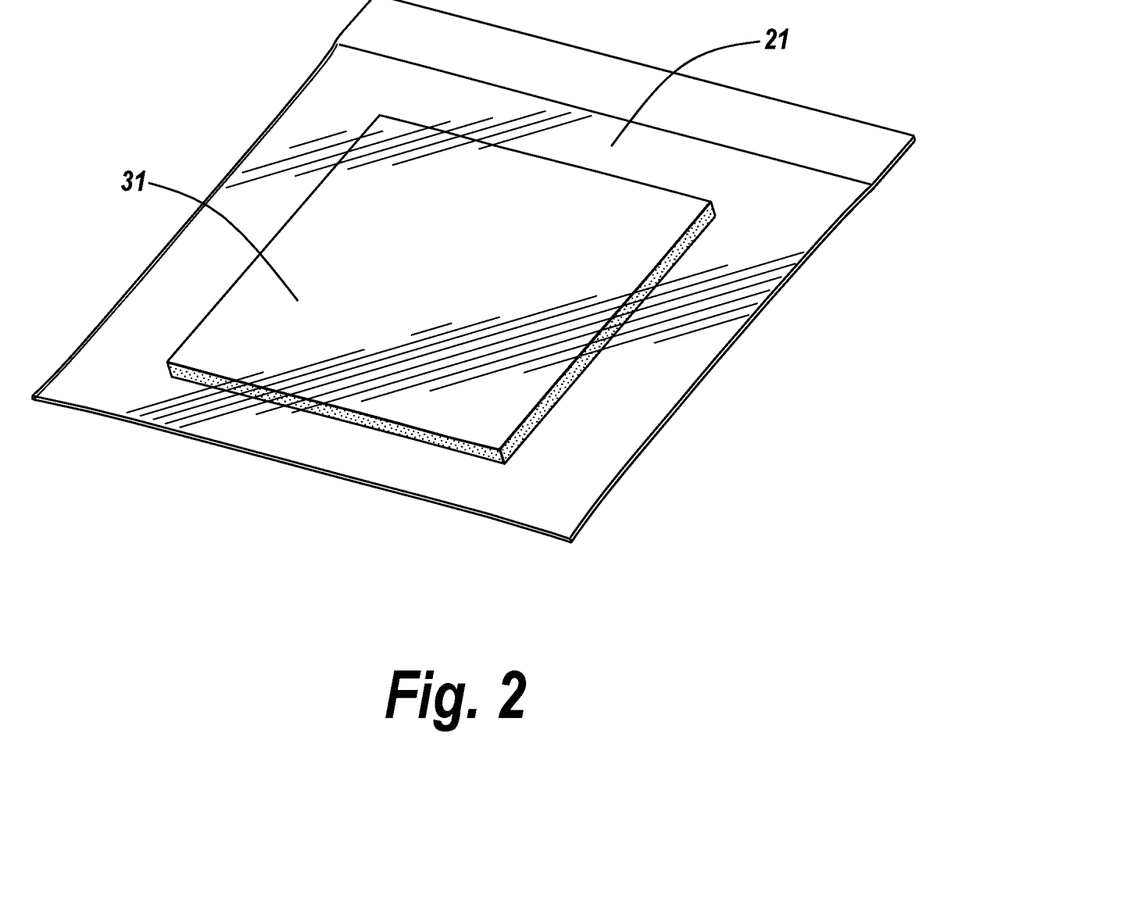
FIG. 2 depicts a tissue wrap embodying features of the present invention.
Figure 3:
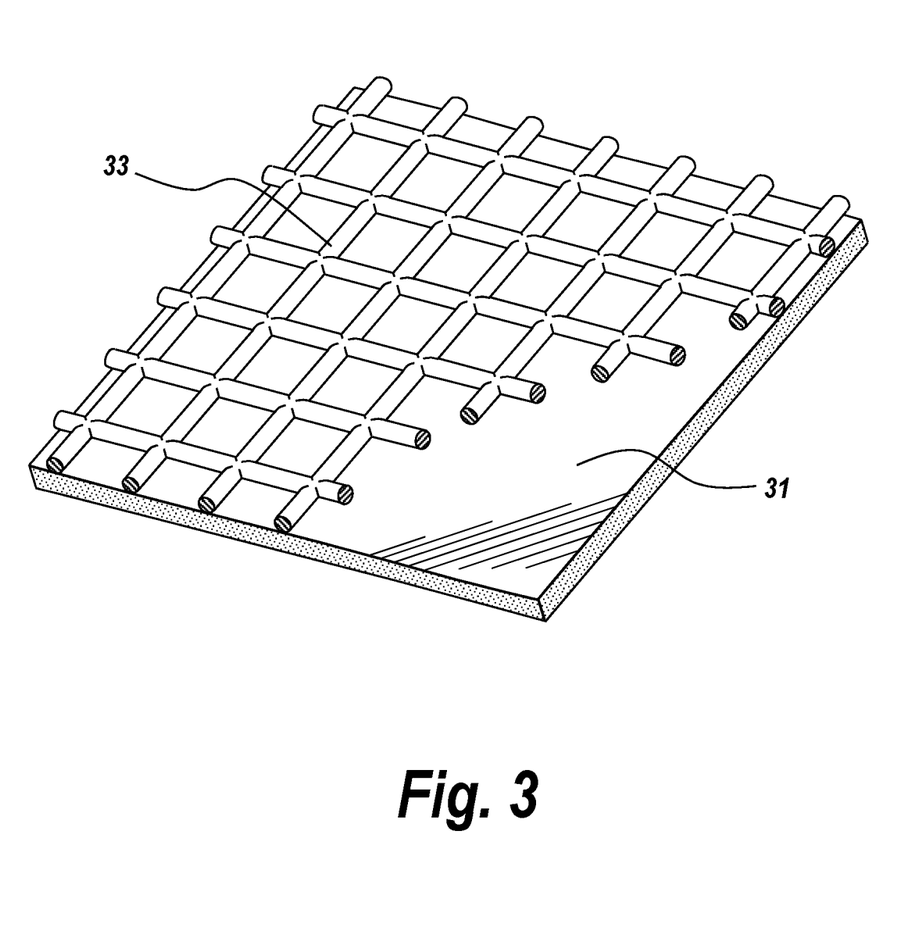
FIG. 3 shows a tissue wrap embodying features of the present invention in a container; and, FIG. 4 depicts a tissue wrap having facial contours and shape embodying features of the present invention.

Turning now to FIG. 2 the container for tissue wrap 21 is depicted as a transparent bag through which the tissue wrap designated by numeral 31 can be seen. As seen in FIG. 3, tissue wrap 31 is formed by affixing amnion tissue to a first support 33 on one side of the amnion and a second support on the other side of the amnion [not shown] and air drying the tissue for thirty minutes to three hours or more, based on humidity, and, most preferably, for about one hour. The supports, of which first support 33 is depicted, maintain the shape of the tissue during the drying process. The supports are preferably removed prior to placement of the tissue in container 21. One embodiment of the present invention features a first support 33 and second support constructed and arranged to have facial features [not shown]. The first support 33 and the second support are sculpted to resemble a human face in shape and contour such that the tissue wrap 21, when placed on the face of a subject will readily conform to the shape and contours of the subject's face as best seen in FIG. 4.

Figure 4:
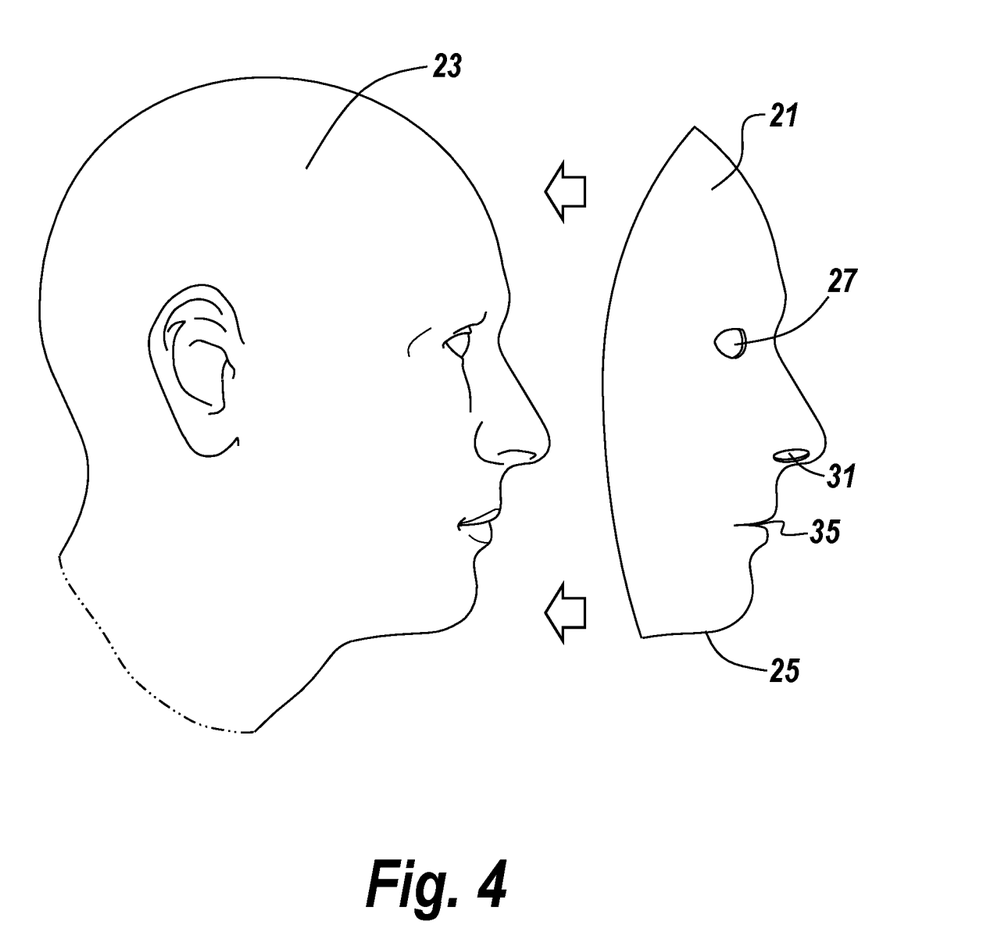

FIG. 4 depicts a subject 23 to which a tissue wrap 21 in the form of a mask 25 is being applied. Mask 25 has openings 27 (only one is visable) for the eyes and openings 31 (only one is visable) for nasal passages and an opening 35 for the mouth. Mask 25 is removed from the container and placed over the face to create a cosmetic result.

Returning now to FIG. 1, the dried particulate mixture is obtained from the mechanical decellularization or cryofractionation of about $1.5 \times 10^{-2}$ cm$^3$ to $5 \times 10^{-2}$ cm$^3$ of amnion/mL of reconstituted medicament and include particles greater than 20-100 microns in diameter. Upon reconstitution of the dried particulate mixture by suspension in a solution of amniotic fluid and/or PlasmaLyte A™, the reconstituted medicament can be administered to the subject animal to promote the healing of superficial wounds.

The dried particulate mixture obtained from the cryofractionation comprises about $1.5 \times 10^{-2}$ cm$^3$ to about $5 \times 10^{-2}$ cm$^3$ of amnion/mL of reconstituted medicament.

The fetal cells can comprise amniotic fluid cells and the particulate matter can be filtered to contain particles that are less than 100 microns in diameter. The fetal cells can have a concentration from $10^3$ to $10^{20}$/mL mesyschimal and/or epithelial stem cells. In another embodiment, fetal cells can have a concentration of $10^3$ to $10^{12}$/mL. In another embodiment, fetal cells can have a concentration of $10^4$ to $10^{12}$/mL. In another embodiment, fetal cells can have a concentration of $10^4$ to $10^{11}$/mL. In another embodiment, fetal cells can have a concentration of $10^4$ to $10^{10}$/mL. In another embodiment, fetal cells can have a concentration of $10^4$ to $10^9$/mL. In another embodiment, fetal cells can have a concentration of $10^4$ to $10^8$/mL. In another embodiment, fetal cells can have a concentration of $10^4$ to $10^7$/mL. In another embodiment, fetal cells can have a concentration of $10^4$ to $10^6$/mL. In another embodiment, fetal cells can have a concentration of $10^3$ to $10^6$/mL. In another embodiment, fetal cells can have a concentration of $10^3$ to $10^7$/mL.

In one example, the fetal cells can have a concentration of about $0.8 \times 10^6$ to $1.2 \times 10^6$ cells/mL of the particulate cellular suspension. The dried particulate mixture can contain particles obtained from the cryofractionation of from about $1.5 \times 10^{-2}$ cm$^3$ to about $5 \times 10^{-2}$ cm$^3$ amnion per mL of the particulate cellular suspension. In one example, the particulate cellular suspension comprises a particulate matter obtained from the cryofractionation about $1.5 \times 10^{-2}$ cm$^3$ to about $5 \times 10^{-2}$ cm$^3$ amnion for every $10^6$ plus or minus $2 \times 10^5$ amnion fluid cells.

Features of the present invention are further described with respect to the following Examples. These examples feature equine subjects and materials. However, materials derived from other animals species, for example, without limitation, canine, feline, bovine, porcine and other animal species materials and subjects can be prepared in a similar manner as outlined below. The equine materials have been utilized with avian, reptilian and other animal groups.

EXAMPLES

Example 1: Amniotic Material Processing

This procedure defines the aseptic collection of amniotic material (amnion and amniotic fluid) for injection at the site of an injury.

Amnion Tissue

The amnion container was picked up and sampled for Bioburden. The amnion was aseptically transferred into the sterile field (laminar flow hood). The amnion transport packaging (previously disinfected, i.e. with 70% ETOH) was opened.

A 50 mL sample of the Amnion Transport Solution was aseptically transferred into a 30 to 60 mL conical tube for pre-processing bioburden testing. The vial was labeled with sample description, batch number, date and time and placed in a designated refrigerator.

(1) Amnion Preparation

The amnion from the incoming container was transferred into approximately 200 mL of Plasma Lyte-A in a sterile bioassay dish where it was gently rinsed. A piece of amnion was then spread evenly on a sterile cutting board carefully avoiding any overlaps. A record was made of the amnion preparation start time. Sterile gauze or laps were used to remove any remaining debris/blood from the surface of the amnion. The amnion was inverted and the surface of the opposite site was similarly washed. Any chorion was removed by blunt dissection to separate it from the amnion. After washing and cleaning, the amnion pieces were returned to the bioassay dish containing Plasma Lyte-A. Using a sterile scissors/scalpel, the amnion was cut into 2 to 10 sections. The approximate area of each piece (50-450 cm$^2$) was measured and recorded using a sterile stainless steel ruler.

The cleaned pieces of the amnion were placed back on the sterile cutting board and the amnion was spread out on the board taking care to not overlap. A sterile nylon mesh was placed over the surface of the amnion again taking care to overlap them. The amnion and mesh were then placed onto a sterile drying rack and allowed to air dry for a minimum of one hour. Start and stop times for drying were recorded.

(2) Amniotic Fluid (a) Amnion Fluid Preparation

A large sterile pan was first placed into the sterile field (laminar flow hood) and filled with cold packs from a −80° C. freezer. The aspiration containers with the amniotic fluid were disinfected with 70% ethanol (ETOH), inspected for integrity and placed on the cold packs in the laminar flow hood. The source of the amniotic fluid was confirmed by looking at the Donor animal ID number. The 2.0 mL of amniotic fluid was then aseptically pipeted into a 2 mL sterile microcentrifuge tube for bioburden testing. The vial was labeled with the sample number, batch number, date and time and placed in the designated refrigerator.

Using a 50 mL sterile disposable serological pipette all the remaining amniotic fluid was transferred into 1 liter sterile disposable bottles and placed on the cold pack. The total volume of the amniotic fluid and the color were recorded.

(3) Amniotic Fluid Cell Count and Determination of the Number of Viable Cells

Each amniotic fluid bottle was gently mixed and 1.0 mL of the fluid was collected using a 1 mL micropipette and transferred into a 2 mL Eppendorf microcentrifuge tube. A total of 50 of cell suspension was then added to 50 μL of trypan blue (0.4%) in an Eppendorf microcentrifuge tube and vortexed for 5 seconds. The sample was placed on a rack for 5 minutes.

A Neubauer chamber (hemocytometer) was rinsed with distilled water, and then sprayed with ETOH 70% and wiped clean and dried with paper towels. A cover slip was placed on the top of the micro-grids of the chamber. The trypan blue-cell suspension was gently mixed and used to fill both sides of the hemocytometer with 10 μL by capillary action. The cells were allowed to settle down for at least 30 seconds. The hemocytometer was placed under the microscope and all cells in the four 1 mm corner squares and one 1 mm center square were counted. For accuracy the total number of cells counted was greater than 100. The cells were re-counted if >10% of the cells appeared clustered, by vigorously pipetting in the original cell suspension as well as in the trypan blue cell suspension mixture. Using a double cell counter, the number of viable and non-viable cells was determined. The cells in both chambers were counted and an average was calculated. For the trypan blue test, live cells did not take up the dye, whereas dead (non-viable) cells did. Thus non-viable cells stained blue and viable cells remained opaque. "Ghost" cells, which appeared as flattened pale blue cells were not counted.

The number of cells was determined as follows: Each square represented a total volume of $0.1 \text{ mm}^3$ or $1 \times 10^{-4}$ mL (0.1 mm depth×1 mm width×1 mm height=$0.1 \text{ mm}^3$). The number of cells per mL was then deduced from the average viable cell count per 1 mm square×$2 \times 10^4$. The total cell number was therefore equal to the number of cells per mL multiplied by the original volume of sample fluid. The cells were then diluted to the desired concentration.

Example 2: Aseptic Processing of the Amniotic Material (1) Aseptic Cryofractionation of Amnion After at least one hour, the amnion was removed from the drying rack and transferred into the milling chambers having an impactor. The milling chambers were placed into the Cryomill and cryofractionated using the following settings:
Number of Cycles: 4
Frequency 1/s: 10 CPS_
Precooling Time: 10 minutes
Grinding Time: 4 minutes
Intermediate Cooling: 3 minutes Once grinding was complete, the milling chambers were allowed to warm to room temperature for approximately two hours. The start and stop times were recorded.

Approximately 50 mL of the amnion suspension solution was dispensed into each milling chamber. The inside milling chamber and the impactor were rinsed with the solution multiple times until the ground amnion (dried particulate mixture) was re-suspended and collected in the bottom of the chamber. The impactor was removed using the magnet pen. The cryofractionated amnion solution was then transferred to the amnion suspension container and placed on cold packs in the sterile field and diluted to the desired amount.

(2) Aseptic Processing of Amniotic Fluid

The amniotic fluid was aliquoted evenly into 50 mL sterile centrifuge tubes and centrifuged at 200-400×g (1100-1600 rpm) for approximately 5-10 minutes at room temperature. The supernatant was then removed from each tube using a 25 mL sterile serological pipette. The amniotic liquid was kept in new container and the pellet was re-suspended in Plasma Lyte-A™ to a total volume of 25 mL in each tube. The re-suspended cells in any two different tubes were vortexed for approximately 3 to 5 sec and consolidated into a single tube prior to centrifugation at 200-400×g (1100-1600 rpm) for approximately 5-10 minutes at ambient temperature. The preceding steps were repeated as necessary.

The supernatant from each tube was removed using a sterile pipette and the pellet was again re-suspended in a cell suspension solution (amniotic fluid and/or an isotononic solution, e.g., PlasmaLyte A™) to bring the volume in each tube to about 10 mL and vortexed for approximately 3 to 5 seconds. A 1 mL aliquot was removed and the cell count and viability was determined using the above-described trypan blue test.

If red blood cells were present in the amniotic fluid cell suspension, they were removed using a RBC Lysing Solution. A 10× concentration was prepared as follows: $NH_4Cl$ (ammonium chloride)=8.02 gm+$NaHCO_3$ (sodium bicarbonate)=0.84 gm adjusted to a total volume of 100 mL with Millipore filtered water. 10 mL of the 10× concentrate was added to 90 mL Millipore filtered water and refrigerated until use. The amount needed of Erythrolysis solution (15 mL per tube centrifuged) was removed from the refrigerator and kept for a period of 0.5 hours in the stabilization incubator. After centrifuging the amniotic fluid at 400×g for 10 minutes, the supernatant was removed and the pellet was re-suspended in Erythrolysis solution (minimum of 50 mL per tube). The contents of all the tubes were consolidated into one tube that was rocked for ~10 minutes at room temperature until the liquid was clear red. The cells were again centrifuged for 5 minutes at 250 to 400×g. The supernatant was decanted. The pellet was washed with 50 mL of PBS or PlasmaLyte A™ before centrifugation again for 10 minutes at 250 to 400×g. The washing of the pellet was repeated as needed. The amniotic fluid cells were then filtered through a 100 μm cell strainer, and re-suspended in PBS or PlasmaLyte A™. The cells were again centrifuged for 10 minutes at 250 to 400×g. The supernatant was decanted and the pellet was left in the 50 mL conical centrifuge tube.

(3) Procedure for Cryopreservation of Cryofractionated Amnion with Amnion Fluid Cells Appropriate size cryovials that were previously labeled and their corresponding size of CoolCell™ freezer (CCF) racks were placed in the hood. CryoStor 10™, the Cell Suspension Solution and the Amnion Suspension Solution were also placed on cold packs in the hood. Cryostor 10™ is commercially available from Biolife Solutions.

The cell suspension solution and the amnion suspension solution were then combined into the cell suspension solution container. Using 50 mL serological pipettes, the solutions were homogenized several times. The container was again placed on the cold packs on the sterile field. Empty cryovials were placed in the CCF racks on cold packs and their caps were removed inside the hood (sterile field). The mix of cell/amnion suspension solution was pipeted into an empty Amnion Suspension container and a same volume of CryoStor 10™ was added and homogenized before being placed on the cold packs. A 50 mL pipette Combitip was fitted on to a repeat pipetor set to dispensing mode. The fill volume was adjusted and 50 mL of the Cell/Amnion solution was aspirated and then adjusted to the desired dispense volume (1 or 2 mL). The cryovials in the CCF were then filled and the vial caps were replaced securely and the rack of filled vials was placed on cold packs for QC inspection.

Cell freezing was achieved by cooling the cells at a cooling rate of 1° C. per minute from 4° C. to −80° C., using a passive cooling controlled-rate freezer CoolCell™ (commercially available from Biocision.)

The cell suspension in cryoprotective freezing medium was aliquoted into each of the cryovials and the cells were gently mixed to maintain a homogeneous cell suspension. The solid core of the CoolCell (black ring) at room temperature was seated in the bottom of the central cavity and the vials containing the cell suspension were placed in each well. The lid of the CoolCell™ was fully sealed and the Coolcell™ was placed into a −80° C. freezer for at least 4 hours prior to transfer on dry ice to long term storage. Cell viability and QA/QC were evaluated by thawing one vial after short term storage.

Example 3: Amniotic Tissue Wrap Preparation

After confirming the amniotic tissue source and donor mare ID and recording the time of receipt, the amnion transport packaging (previously disinfected, i.e. with 70% ethanol, methanol, etc.) was aseptically transferred into the sterile field (a laminar flow hood). A sample of the Amnion Transport Solution was first transferred into a 50 mL conical tube for Bioburden testing. The vial was then labeled with sample description, batch number, date and time and placed in designated refrigerator.

(1) Amniotic Membrane Wrap Preparation

Saline was aseptically added into a second receiving pan in the sterile field (i.e. laminar flow hood) and the amnion tissue was taken from incoming receiving pan to the second receiving pan containing the sterile saline. Any remaining blood was rinsed with sterile saline. After documenting the amnion preparation start time, sterile gauze or laps was used to remove any remaining debris/blood from the surface of the amnion. The amnion was then inverted and the other side was rinsed and washed. Any remaining chorion was removed by blunt dissection to separate it from the amnion. The amnion was kept wet with sterile saline. The tissue was blocked off by cutting away any stringy ends and checked for holes or tears. After repositioning the amnion on the cutting board with the chorion side up, the approximate area of each piece of amnion was measured and recorded in $cm^2$ using a sterile stainless steel ruler.

The amnion (chorion side up) was covered with a sterile mesh (e.g., a nylon mesh) wetted with sterile saline. For the purpose of this discussion, there is a first steel mesh which is denoted by a first visible indicia, the color white, and a second steel mesh, to be discussed below, which is denoted by a second visible indicia, the color blue. Any reference to the colors white or blue are directed to these visible indicia. Those skilled in the art will recognize that such visible indicia is matter of choice. The mesh was cut to size and was allowed to slightly overlap the amnion. The mesh-covered amnion was then gently lifted, turned over and placed back on the cutting board. Caution was used as to not disturb the mesh/amnion interface. The newly exposed side of the amnion was wiped with sterile wipes or gauze pads to remove any remaining blood or small tissue particles. The newly exposed side of the amnion was covered with a second steel mesh, BLUE sterile mesh (e.g., a nylon mesh) wetted with sterile saline. The mesh was cut to size and was allowed to slightly overlap the amnion.

The amnion tissue sandwiched between the white and blue mesh was placed on the drying rack where the amnion tissue was allowed to dry for 60 to 90 minutes at ambient temperature (65° to 70° F.). Caution was used as to not disturb the mesh/amnion interface. The amnion was kept unfolded and as flat as possible during this step. Additional drying racks were used as needed. The total drying time was recorded. The dried tissue was then removed from the rack(s) and laid flat on the cutting board, WHITE side up. The WHITE mesh was carefully removed from the entire sheet of amnion which was checked for holes or tears. With the BLUE mesh side up on the cutting board, each section was cut using a scalpel or rotary cutting blade and the sizes and surface areas were recorded as 5×5 cm, 10×10 cm, round 15 mm diameter and round 22 mm diameter. Those skilled in the art will recognize that the sections can be cut and sized to fit particular needs and these sizes and shapes are only exemplary. For example, the supports may be constructed and arranged to resemble faciual features to produce a mask as previously described.

(2) Amniotic Membrane Wrap Pre-Packing Pouches, Sealing Test and Labeling

The sterile field was set up for packaging including a sealer for packing pouches (Sealer settings: Temperature=177±9° C. (350±15° F.)). Three (3) empty pouches were sealed for visual inspection and retention and then labeled. Packing pouches are available from numerous vendors. One suitable pouch is sold under the trademark KAPAK™.

Amniotic Membrane Wrap Packing

Pouches were transferred onto the sterile field (previously disinfected laminar flow hood). Using sterile forceps, each individual tissue membrane was inserted into the inner pouch. Large membranes were folded if necessary. The pouches were sealed with the dried amnion tissue on a mesh (see, for example, FIGS. 2 and 3) and inspected for a broken seal, impurities, and defects. Upon passing the inspection, the pouches were labeled with date and packaged in large pouches according to size and stored in the refrigerator or at room temperature. The donor ID, size, date, time, and initials were documented.

Example 4: Implantation of Cryofractionated Amnion and Isolated Amniotic Fluid Cells (1) Thawing Vials A container was ¾ filled with hot tap water with a thermometer and cold water was added until a temperature of 37° C. was reached. A vial of cryofractionated amnion with amniotic fluid cells was taken from the −80° C. freezer. Holding the cap, the vial was partial immersed in the water bath for approximately 2 to 3 minutes with gentle agitation until the contents were melted. The vial was removed from the water bath and the exterior was wiped with sterile gauze saturated with 70% ethanol. The thawed contents were then ready for immediate use.

(2) Implantation Procedure

The site for the product implantation would be processed as a surgically prepared area. After cleaning or clipping of any gross contamination, the complete the area would be scrubbed with chlorhexidine for 5 to 7 minutes and then wiped down with alcohol swabs. Before proceeding, the area would be cleaned until the alcohol swabs used on the scrubbed area were dirt-free. Antibiotics would be administered prior to starting the procedure, if needed.

The contents of the 2 mL vial would be split into multiple doses (0.50 to 0.67 mL) and loaded into syringes (for example, 1 mL syringes) with sterile hypodermic needles (for example 22 gauge, 1.5 inch needles). The sites comprising creases, wrinkles, inconsistent pigment, sags, hair loss, spots, loss of flexibility, thinning, and voids are injected with small volumes of combined aesthetic modifier. After injection, the site was bandaged with sterile swabs and adhesive bandage, if needed.

Example 5: Implantation of Cryofractionated Amnion and Isolated Amniotic Fluid Cells in Combination with the Amnion Tissue Wrap (1) Materials A kit comprising sterile hypodermic needles (18 and 23 gauge), syringes (3 to 5 mL), vials of thawed cryofractionated amnion and amniotic fetal cells as well as packaged amnion tissue wrap of the appropriate size were assembled (see FIG. 1) together with sterile gloves, 1% lidocaine, saline and sedatives and/or anesthetics.

(2) Surface Preparation

The site would be initially pre-cleaned to remove dirt, scrubbed with chlorhexidine for 5 to 7 minutes and then wiped down with alcohol swabs.

(3) Inflammation:

A subject would create a mild inflammatory response by applying one or more inflammation means comprising keratolytics, irritants, rubefacients, abrasives, phototherapy, dermal microneedle devices prior to or during administration of the aesthetic modifier. The one or more keratolytics, irritants, rubefacients, or abrasives are carried in a spray, cream, ointment, slurry, paste, wash, mask, dermal patch, powder, solution or suspension. The one or more keratolytics, irritants, rubefacients, or abrasives are applied before or carried with with the aesthetic modifier and applied with the aesthetic modifier. Irritants, rubefacients and vesicants are know in the art and include, by way of example, without limitation, anthralin, camphor, cantharidin, *capsicum*, coal tar, ichthammol, juniper tar, menthol, Peruvian balsam, and pine tar. Keratolytics are known in the art and include by way of example, without limitation, benzoyl peroxide, salicylic acid, retinoic acid and other vitamin A derivatives. Keratolytic compounds are commonly found in acne treatment products. The kit 11 may also comprise photo or light devices to create an inflammatory response. Photo or light devices are known in the art as sun lamps and tuned lazer devices.

This step created a relatively clean wound bed and generated an inflammatory signal that induced the migration and proliferation of stem cells and growth factors (from the amniotic material and subject's own immune system). Systemic antibiotics were administered prior to starting the procedure.

(4) Application of Amniotic Tissue Wrap

Amniotic tissue wrap shaped as a mask for facial application would be applied to the face of the subject.

After the application of the amnion tissue wrap as described above, the approximate volume of the would be estimated and the amount of cryofractionated amnion and isolated amnion fluid cells to be injected were determined in accordance with guidelines shown in Table 3.

TABLE 3

Amount of cryofractionated amnion and isolated amnion fluid cells to be injected as a function of volume crease or voids or wrinkles.

| Area | Amount of cryofractionated amnion/ amnion fluid cell suspension to use |
|---|---|
| <12.5 cm² | 1.0 mL |
| >12.5 cm² but <25 cm² | 1.5 mL |
| >25 cm² | 2.0 mL |

After application of the inflammation means, the cryofractionated amnion/amnion fluid cell suspension would be injected into the skin below the features which modification is desired.

To minimize discomfort and to ensure an adequate spread of the amniotic material, the cryofractionated amnion/amnion fluid cell suspension would be mixed with 1% plain lidocaine in a 1:1 ratio. After the completion of the procedure, the site was dressed with a nonporous dressing followed by application of a nonstick dressing and a dry sterile dressing of gauze. Five to seven days after implant of the amnion allograft, the area would be redressed, and standard wound care consisting of saline wet to dry sterile gauze dressing would be resumed.

Any patent, patent application, publication, or other disclosure material identified in the specification is hereby incorporated by reference in its entirety and for all purposes to the same extent as if each such individual reference (e.g., patent, patent application, publication, or other disclosure material) was specifically and individually indicated to be incorporated by reference in its entirety for all purposes. Any material, or portion thereof, that is said to be incorporated by reference herein, but which conflicts with existing definitions, statements, or other disclosure material set forth herein, is only incorporated by reference to the extent that no conflict arises between that incorporated by reference material and the present disclosure material.

Other embodiments are within the following claims.

We claim:

1. An article of manufacture comprising a dried particulate mixture of decellularized fetal tissue obtained from one or more animals compatible with a subject, the dried particulate mixture of decellularized fetal tissue configured for modifying a feature of the subject and capable of reconstitution to form a reconstituted modifier having fractionated the dried particulate mixture of decellularized fetal tissue that is filtered for particles <70 microns, the reconstituted modifier comprising a biocompatible solution, the reconstituted modifier comprising an inflammation inducing means comprising at least one of anthralin, camphor, cantharidin, *capsicum*, coal tar, ichthammol, juniper tar, menthol, Peruvian balsam, pine tar, benzoyl peroxide, salicylic acid, retinoic acid or a vitamin A derivative wherein the reconstituted modifier is configured for transdermal administration to the subject to produce at least one of fewer wrinkles, fewer creases, shallower wrinkles, shallower creases, less sagging, tighter skin, fuller skin, thicker skin, more flexible skin, more uniform coloration, fewer spots on the skin, smaller spots on the skin or lighter spots on the skin.

2. The article of manufacture of claim 1, wherein said fetal tissue is decellularized by cryofractionation.

3. The article of manufacture of claim 1, wherein said fetal tissue comprises at least one of amnion or chorion, and the amnion is subject to diafiltration by centrifuging the amnion through dialysis membranes with a pore size of 70 microns.

4. The article of manufacture of claim 1, wherein said dried particulate mixture includes $10$-$10^{20}$ cells per mL prior to cryomilling.

5. The article of manufacture of claim 1, wherein the particulate mixture is reconstituted by suspension in a sterile, non-pyrogenic isotonic solution, and wherein the fetal tissue is turned into gelatin and added to the reconstituted modifier.

6. The article of manufacture of claim 5, wherein injection of the reconstituted modifier promotes filling of voids and creases in the skin.

7. The article of manufacture of claim 1, wherein the dried particulate mixture volume of $1.5 \times 10'$ cm³ to about $5 \times 10'$ cm³ is suspended to give 1 ml total volume of the reconstituted modifier.

8. The article of manufacture of claim 1, wherein the particulate mixture is reconstituted by suspension in a sterile, non-pyrogenic isotonic solution and/or amniotic fluid to form the reconstituted modifier.

9. The article of manufacture of claim 1, wherein the particulate mixture is reconstituted by suspension in a solution of amniotic fluid.

10. The article of manufacture of claim 1, further comprising fetal cells.

11. The article of manufacture of claim 1, wherein the dried particulate mixture includes a concentrate of exosomes from the fetal tissue added to the reconstituted modifier.

12. The article of manufacture of claim 1, wherein the reconstituted modifier is applied as a cream, ointment, slurry, paste, wash, mask, dermal patch, spray, powder, solution or suspension to the skin of a subject or into a dermal layer of the skin of a subject.

13. An article of manufacture comprising
a mixture comprising:
- a decellularized fetal tissue obtained from one or more animals, the decellularized fetal tissue having been filtered for particles <70 microns; and
- a base comprising at least one of a cream base, an ointment base, a lotion base, or a paste base and further comprising an inflammation inducing means comprising at least one of anthralin, camphor, cantharidin, *capsicum*, coal tar, ichthammol, juniper tar, menthol, Peruvian balsam, pine tar, benzoyl peroxide, salicylic acid, retinoic acid or a vitamin A derivative, wherein the mixture is configured for administration to the subject to produce at least one of fewer wrinkles, fewer creases, shallower wrinkles, shallower creases, less sagging, tighter skin, fuller skin, thicker skin, more flexible skin, more uniform coloration, fewer spots on the skin, smaller spots on the skin or lighter spots on the skin.

* * * * *